United States Patent [19]

Bille et al.

[11] Patent Number: 5,246,435
[45] Date of Patent: Sep. 21, 1993

[54] METHOD FOR REMOVING CATARACTOUS MATERIAL

[75] Inventors: Josef F. Bille, Heidelberg, Fed. Rep. of Germany; David Schanzlin, St. Louis, Mo.

[73] Assignee: Intelligent Surgical Lasers, San Diego, Calif.

[21] Appl. No.: 841,614

[22] Filed: Feb. 25, 1992

[51] Int. Cl.$^5$ ...................... A61B 17/00; A61B 17/32
[52] U.S. Cl. .......................................... 606/6; 606/4; 128/898
[58] Field of Search ................ 128/395, 898; 606/4–6, 606/107, 166, 10–12; 604/21

[56] References Cited

U.S. PATENT DOCUMENTS

| | | | |
|---|---|---|---|
| 3,653,384 | 4/1972 | Swope | 128/303.1 |
| 3,720,213 | 3/1973 | Hobart et al. | 128/395 |
| 3,769,963 | 11/1973 | Goldman et al. | 128/2 R |
| 3,783,874 | 1/1974 | Koester et al. | 128/303.1 |
| 3,821,510 | 6/1974 | Muncheryan | 219/121 L |
| 3,828,788 | 8/1974 | Krasnov et al. | 128/303.1 |
| 3,843,865 | 10/1974 | Nath | 219/121 L |
| 3,942,519 | 3/1976 | Shock | 128/24 A |
| 3,971,382 | 7/1976 | Krasnov | 128/303.1 |
| 3,982,541 | 9/1976 | L'Esperance, Jr. | 128/303.1 |
| 3,992,682 | 11/1976 | White et al. | 331/94.5 |
| 4,024,866 | 5/1977 | Wallach | 128/276 |
| 4,053,845 | 10/1977 | Gould | 330/4.3 |
| 4,069,823 | 1/1978 | Isakov et al. | 128/303.1 |
| 4,091,274 | 5/1978 | Angelbeck et al. | 250/201 |
| 4,091,814 | 5/1978 | Togo | 128/303.1 |
| 4,122,853 | 10/1978 | Smith | 128/303.1 |
| 4,161,436 | 7/1979 | Gould | 204/157.1 |
| 4,207,874 | 6/1980 | Choy | 128/6 |
| 4,210,400 | 7/1980 | Misek | 356/359 |
| 4,309,998 | 1/1982 | Aron et al. | 128/303.1 |
| 4,311,147 | 1/1982 | Hausler | 128/328 |
| 4,391,275 | 7/1983 | Frankhauser | 128/303.1 |
| 4,408,602 | 10/1983 | Nakajima | 128/303.1 |
| 4,409,979 | 10/1983 | Roussel et al. | 128/303.1 |
| 4,452,517 | 6/1984 | Kohayakawa | 351/206 |
| 4,469,098 | 9/1984 | Davi | 128/303.1 |
| 4,477,905 | 10/1984 | Sweeney | 372/25 |
| 4,499,897 | 2/1985 | Roussel | 128/303.1 |

(List continued on next page.)

FOREIGN PATENT DOCUMENTS

| | | |
|---|---|---|
| 2538960 | 4/1977 | Fed. Rep. of Germany . |
| 2913251 | 10/1980 | Fed. Rep. of Germany . |
| 3146626 | 6/1983 | Fed. Rep. of Germany . |
| 87/07165 | 12/1987 | PCT Int'l Appl. . |
| 2108282 | 8/1982 | United Kingdom . |

OTHER PUBLICATIONS

Bille, J. F. et al. *3D Imaging of the Human Eye Using the Laser Tomographic Scanner LTS.* Dept. of Ophthalmology, UCSD, La Jolla Calif.

Claflin, E. Scott et al. *Configuring an Electrostatic Membrane Mirror by Least-Squares Fitting with Analytically derived Influence Functions.* Opt. Soc. Am. A., vol. 3, No. 11, Nov. 1986, pp. 1833–1839.

*The Coaxial Position of the Optical Elements.* Optics, pp. 134–139.

(List continued on next page.)

Primary Examiner—Stephen C. Pellegrino
Assistant Examiner—Mike Peffley
Attorney, Agent, or Firm—Nydegger & Associates

[57] ABSTRACT

A method for using an ophthalmic laser system to remove cataractous tissue from the lens capsule of an eye requires phacofragmentation of the lens tissue and subsequent aspiration of the treated tissue. More specifically, a cutting laser is used to create various strata of incisions through the lens tissue. Within each stratum, each incision is made in the direction from a posterior to an anterior position. The strata are stacked on each other in the posterior-anterior direction, and each includes a plurality of minute incisions. The most posterior stratum of incisions is created first by referencing the cutting laser back into the lens tissue from the posterior capsule. Subsequent, more anterior strata, are created by referencing the cutting layer from the tissue treated by the previous stratum of incisions. In each stratum, the vapors which result from the incisions are allowed to infiltrate between the layers of the lens tissue to fragment and liquify the tissue. The liquified lens tissue is then aspirated.

23 Claims, 2 Drawing Sheets

U.S. PATENT DOCUMENTS

| | | | |
|---|---|---|---|
| 4,503,854 | 3/1985 | Jako | 128/303.1 |
| 4,517,980 | 5/1985 | Tagnon | 128/395 |
| 4,538,608 | 9/1985 | L'Esperance, Jr. | 128/303.1 |
| 4,559,942 | 12/1985 | Eisenberg | 128/303 |
| 4,561,436 | 12/1985 | Munnerlyn | 128/303.1 |
| 4,579,430 | 4/1986 | Bille | 351/206 |
| 4,580,559 | 4/1986 | L'Esperance | 128/303.1 |
| 4,598,311 | 7/1986 | Bellina | 358/93 |
| 4,601,288 | 7/1986 | Myers | 128/303.1 |
| 4,622,967 | 11/1986 | Schachar | 128/303.15 |
| 4,638,800 | 1/1987 | Michel | 128/303.1 |
| 4,665,913 | 5/1987 | L'Esperance, Jr. | 128/303.1 |
| 4,669,466 | 6/1987 | L'Esperance | 128/303.1 |
| 4,704,583 | 11/1987 | Gould | 330/4.3 |
| 4,711,542 | 12/1987 | Ichihashi | 351/221 |
| 4,718,418 | 1/1988 | L'Esperance, Jr. | 128/303.1 |
| 4,727,381 | 2/1988 | Bille et al. | 346/108 |
| 4,732,148 | 3/1988 | L'Esperance, Jr. | 128/303.1 |
| 4,732,473 | 3/1988 | Bille et al. | 356/237 |
| 4,734,557 | 3/1988 | Alfille et al. | 219/121 |
| 4,764,930 | 8/1988 | Bille et al. | 372/23 |
| 4,770,172 | 9/1988 | L'Esperance, Jr. | 128/303.1 |
| 4,773,414 | 9/1988 | L'Esperance, Jr. | 128/303.1 |
| 4,781,453 | 11/1988 | Kobayashi | 351/205 |
| 4,784,135 | 11/1988 | Blum et al. | 128/303.1 |
| 4,881,808 | 11/1989 | Bille et al. | 351/221 |
| 4,901,718 | 2/1990 | Bille et al. | 60/4 |
| 4,907,586 | 3/1990 | Bille et al. | 606/5 |

OTHER PUBLICATIONS

Huber, G. et al. *Room-Temperature 2-um HO:YAG and 3-um ER:YAG Lasers.* Institute fuer Angewandte Physik, University Hamburg.

Krauss, Joel M. et al. *Laser Interactions with the Cornea.* Survey of Ophthalmology, vol. 31, No. 1, Jul.-Aug., 1986, pp. 37-52.

Kuizenga, Dirk J. *FM-Laser Operation of the Nd:YAG Laser.* Journal of Quantum Electronics. vol. 6, No. 11, Nov. 1970, pp. 673-677.

L'Esperance, Francis A. Jr. *Opthalmic Lasers, Photocoagulation, Photoradiation, and Surgery.* Columbia University College of Physicians and Surgeons, New York, N.Y., Second Edition, 1983, pp. 529-538.

Loertscher, Hanspeter. *Noncontact Trephination of the Cornea Using a Pulsed Hydrogen Fluoride Laser.* American Journal of Ophthalmology, No. 104, Nov. 1987, pp. 471-475.

Taboada, J. et al. *Response of the Corneal Epithelium to KrF Excimer Laser Pulses.* Health Physics, vol. 40, May 1982, pp. 677-683.

Trokel, Stephen L. et al. *Excimer Laser Surgery of the Cornea.* American Journal of Ophthalmology, vol. 96, No. 6, Dec. 1983, pp. 710-715.

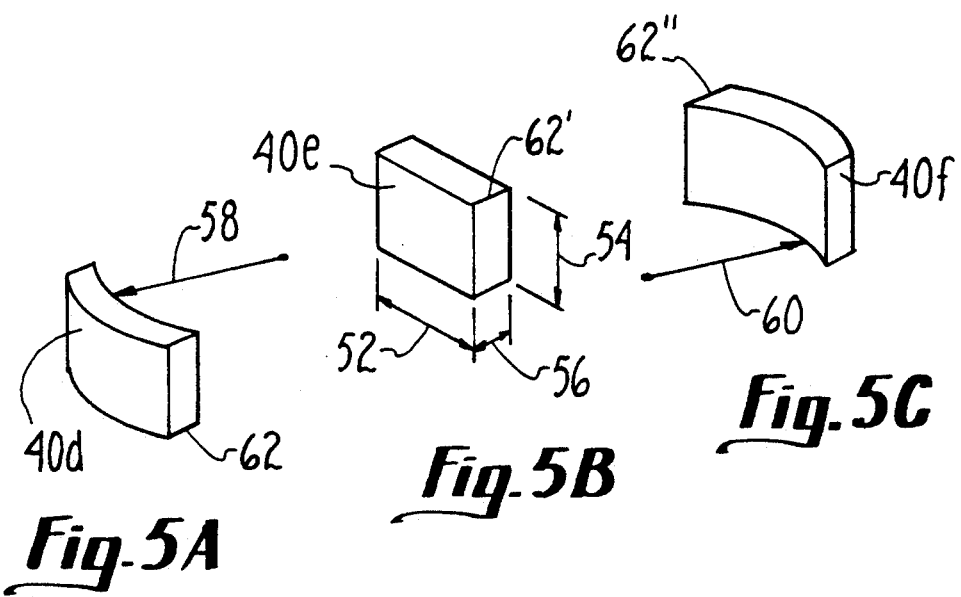
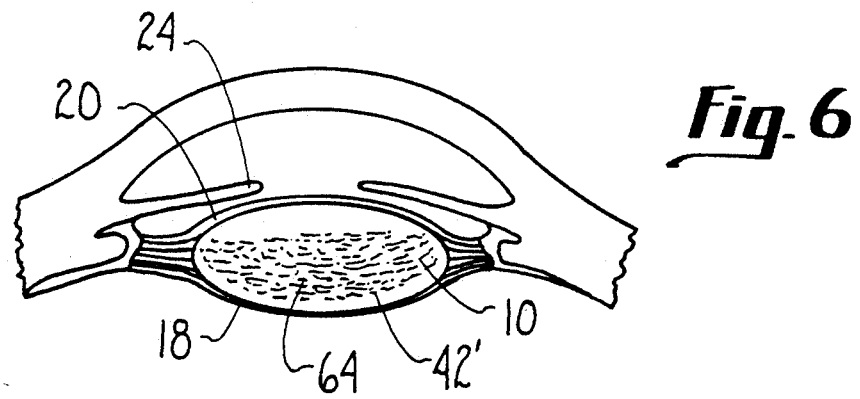
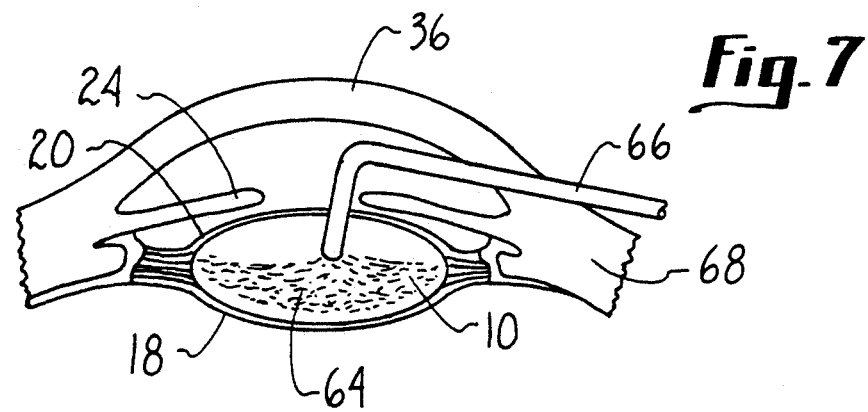

METHOD FOR REMOVING CATARACTOUS MATERIAL

FIELD OF THE INVENTION

The present invention pertains generally to ophthalmic procedures. More particularly, the present invention pertains to a method for using a cutting beam of laser light to photoablate selected tissue of the eye. The present invention is particularly, but not exclusively useful for removing cataractous tissue from the lens capsule of an eye.

BACKGROUND OF THE INVENTION

Although cataracts originate from several different pathologies, their common manifestation is an opacity of the crystalline lens of the eye which either impairs or obstructs the vision of an afflicted individual. In any event, there are several well known cataract surgical procedures which can be performed to alleviate or eliminate the problem. The most radical of these procedures is a lentectomy. In a lentectomy, the opaque crystalline lens is effectively removed from the lens capsule. It is then replaced with an acrylic or plastic lens. Most commonly, the lentectomy is performed by using a knife to cut the lens out of the lens capsule. Recently, however, procedures have been suggested wherein laser energy is used to remove the cataractous tissue from the lens capsule.

U.S. Pat. No. 4,538,608 which issued to L'Esperance, Jr. for an invention entitled "Method and Apparatus for Removing Cataractous Lens Tissue by Laser Radiation" is an example of a device which employs laser energy to perform a lentectomy. According to the teachings of L'Esperance, laser energy is directed onto the anterior aspect of the cataractous lens tissue and the laser beam is then scanned within a limiting perimeter until the cataractous tissue has been photoablated. In accordance with this procedure, the cataractous tissue in the lens is removed in sheets from the anterior aspect of the lens toward the posterior capsule. An adverse consequence of this approach is that it is necessary to continually be working through a fragmented layer of lens tissue which scatters light and thereby causes unwanted inefficiencies.

The present invention, however, recognizes that the anatomy of the lens tissue in the eye, and the reaction of this tissue to photoablation, permits a procedure for removing cataractous tissue from the lens capsule which is quite different from the procedures suggested by L'Esperance. To appreciate this, it is first necessary to understand the anatomy which is being treated.

The lens of an eye is a transparent biconvex body of crystalline tissue which is situated between the posterior chamber and the vitreous body. It is enclosed within a lens capsule and it constitutes part of the refracting mechanism of the eye. The structure of the tissue in the lens includes a lens nucleus which is surrounded by the lens cortex. More specifically, the lens cortex includes separate envelope-like layers of tissue which completely surround the nucleus and all other layers which are located closer to the nucleus. The result is that the lens, in cross section, exhibits an anatomy that structurally appears somewhat like an onion.

As recognized by the present invention, the use of a laser beam to make a plurality of minute incisions throughout the cataractous lens tissue will accomplish at least two results that facilitate the removal of the tissue from the lens capsule. Firstly, such incisions assist in mechanically separating the cataractous lens tissue into small particles. Secondly, the vapors which are released during the photoablation of the incisions will infiltrate between the layers of the lens and will act to liquify the lens tissue. Together, the mechanical separation of the tissue and the tissue liquification process which results from photoablation, appropriately alter the cataractous tissue so that it can be aspirated from the lens capsule.

In light of the above it is an object of the present invention to provide a method for using a laser beam to remove cataractous tissue from the lens capsule of an eye which is accomplished by creating a plurality of minute incisions throughout the cataractous tissue that will separate and liquify the lens tissue to facilitate its removal from the lens capsule. Another object of the present invention is to provide a method for using a laser beam to remove cataractous tissue from the lens capsule of an eye which is accomplished by appropriately confining photoablation within the confines of the lens capsule. Still another object of the present invention is to provide a method for using a laser beam to remove cataractous tissue from the lens capsule of an eye which is accomplished by efficiently using laser energy to photoablate cataractous tissue. Another object of the present invention is to provide a method for using a laser beam to remove cataractous tissue from the lens capsule of an eye which is accomplished by focusing the cutting laser beam through unfragmented tissue to reduce light scattering and improve laser efficiencies. Yet another object of the present invention is to provide a method for using a laser beam to remove cataractous tissue from the lens capsule of an eye which is safely accomplished by continuously referencing the position of each incision into the cataractous lens tissue. Another object of the present invention is to provide a method for using a laser beam to remove cataractous tissue from the lens capsule of an eye which is relatively simple to accomplish and which is comparatively cost effective.

SUMMARY OF THE INVENTION

The present invention pertains to a method for removing cataractous tissue from the lens capsule of an eye. Essentially, this is a two phase procedure wherein the cataractous tissue in the lens capsule is first liquified, and then the liquified tissue is aspirated. According to the present invention, the liquification of the cataractous lens tissue is accomplished using a cutting laser beam.

For the method of the present invention, an ophthalmic laser apparatus is used which focuses a cutting laser beam onto an easily observable reference. Specifically, the reference onto which the cutting laser beam is focused is the cross-over point of a double He-Ne guiding beam. With this arrangement, the operator is able to first position the double He-Ne cross-over as desired, and then expose the focal point of the cutting laser beam onto the cross-over point. The focal point of the cutting laser is then moved in a predetermined manner and along a predetermined path to create an incision into the lens tissue. Each incision is made in a direction for a posterior to an anterior position. By repeating this procedure, the operator selectively makes a plurality of incisions into the cataractous tissue with the cutting laser beam. The vapors which result from these incisions are then allowed to infiltrate between the layers of the lens tissue to further fragment and liquify the tissue. How the incisions are located throughout the cataractous tissue, and the dimensional characteristics of the incision are important for the present invention.

To accomplish the steps of the present invention incisions are made in strata through the lens tissue. More specifically, these various strata can be envisioned as being stacked on top of each other in a posterior-anterior direction. Each stratum includes a plurality of minute incisions having predetermined dimensions. Each incision in each stratum is made in a direction from a posterior to an anterior position. The first stratum to be created is the most posterior of the strata and successively more anterior stratum are then created until all of the cataractous tissue in the lens capsule has been treated.

The first, most posterior, stratum of incisions is created by aiming the cross-over of the double He-Ne guiding beam onto the posterior capsule of the eye. Once the cross-over is so positioned, the laser apparatus is activated by the operator to automatically withdraw the cross-over approximately 100 um into the lens tissue. This locates the double He-Ne cross-over inside the lens tissue adjacent the posterior capsule of the eye. The coincident focal point of the cutting laser is then exposed at the cross-over, and the operator activates the apparatus to make an incision. These steps are repeated as desired by the operator until a strata of incisions have been made adjacent the posterior capsule. It happens that, as the treated tissue liquifies during this process, the refractive characteristics of the treated tissue are changed. This allows the previously liquified stratum to be subsequently used by the operator for referencing the double He-Ne guiding beam.

Subsequent, more anterior, strata are created by referencing the double He-Ne guiding beam from the previously liquified lens tissue. As before, after the operator has positioned the cross-over, an incision can be made. Unlike the procedure for the most posterior strata, however, there is no further need to withdraw the cross-over before making the incision. Again, the operator makes a sufficient number of incisions to create a whole strata of incisions. Each incision in each stratum is made in a direction from a posterior to an anterior position. Additional strata are then created until all of the cataractous tissue in the lens capsule has been liquified.

In accordance with the present invention, each individual incision is made by moving the focal point of the cutting laser beam along a path which begins at a start point and which creates an incision that is approximately two millimeters (2 mm) in length and approximately five hundred microns (500 um) in depth. Further, in order to provide additional protection for the posterior capsule and the anterior capsule from the incisions, the incisions can be curved. In accordance with the present invention, the radius of curvature of the incisions is varied from stratu to stratum. Specifically, these variations are made to transition from an anterior concave curve for incisions in the most posterior stratum, through substantially uncurved incisions in the stratum along the equator of the lens, to an anterior convex curve for incisions in the most anterior stratum. For the present invention the incisions in the most posterior stratum have an anterior oriented radius of curvature of approximately six millimeters (6 mm), while the incisions in the most anterior stratum have a posterior oriented radius of curvature of approximately six millimeters (6 mm).

In addition to changes in the curvature of the incisions, the laser energy used to make the incisions is varied from stratum to stratum. Accordingly, each incision in the most posterior stratum is made using a cutting laser beam having approximately four hundred microjoules (400 uj) of laser energy at its focal point. This level of laser energy for the cutting laser beam is then reduced by approximately seventy-five microjoules (75 uj) for the creation of each successive more anterior stratum of incisions.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 5A is a perspective view of the contained volume of an incision in a posterior stratum;

FIG. 5B is a perspective view of the contained volume of an incision in the equatorial stratum;

FIG. 5C is a perspective view of the contained volume of an incision in an anterior stratum;

FIG. 6 is a cross sectional view of the lens of an eye as seen in FIG. 1 with a liquified posterior layer of cataractous lens tissue; and FIG. 7 is a cross sectional view of the lens of an eye as seen in FIG. 6 with substantially all of the cataractous lens tissue liquified for aspiration.

DESCRIPTION OF THE PREFERRED EMBODIMENTS

Figure 1:
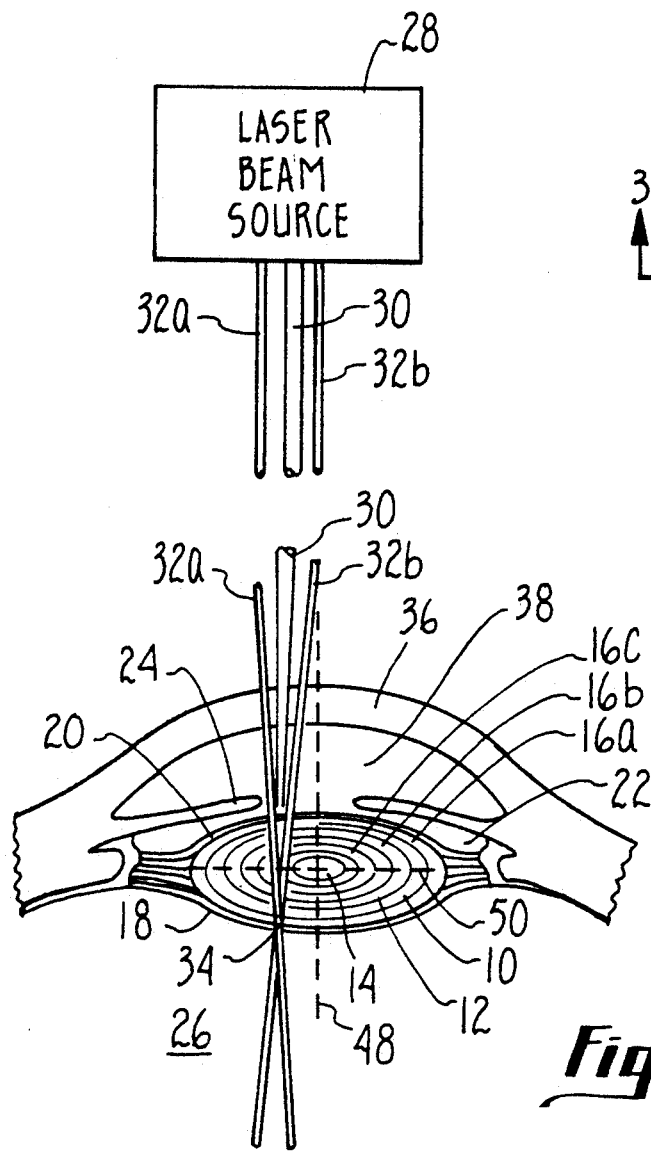
FIG. 1 is a cross sectional view of the lens of an eye, together with its associated anatomy, and a schematic presentation of a laser apparatus operatively positioned in front of the eye.

Referring initially to FIG. 1, a portion of the eye is shown with the lens of the eye designated 10. It is known that the lens 10 includes a cortex 12 which surrounds a nucleus 14, and that both the cortex 12 and nucleus 14 comprise a crystalline tissue. Further, it is known that the cortex 12 is actually a plurality of layers 16 of crystalline lens tissue, of which the designated layers 16 a-c are representative. More specifically, each of the layers 16 completely surround both the cortex 12 and any of the other layers 16 that are located between that particular layer 16 and the cortex 12. The tissue structure of the lens 10 is, therefore, somewhat like that of an onion. FIG. 1 shows that lens 10 is enclosed within a lens capsule which has a posterior capsule 18 and an anterior capsule 20, and that lens 10 is located behind both the posterior chamber 22 and iris 24 of the eye, and in front of the vitreous body 26.

In order to perform the method of the present invention, a laser source 28 is employed. Although several different laser systems can be used to generate a cutting laser beam 30, it is preferable that the laser source 28 be capable of generating pulsed laser beams similar to those disclosed in U.S. Pat. No. 4,764,930 which issued to Bille et al. and is assigned to the same assignee as the present invention. Additionally, it is necessary that the laser source 28 be capable of generating what is commonly referred to as a double He-Ne laser beam 32. The double He-Ne (Helium and Neon) emits light in the visible range. Thus, when the two separate beams 32a and 32b of the double He-Ne are angled with respect to each other, a reflection of their cross-over point 34 can be observed. The cutting laser beam 30 is focused so that its focal point is coincident with the cross-over 34 of the Double He-Ne beam 32. This arrangement allows use of the cross-over 34 to guide the positioning and location of the focal point of the cutting beam 30.

The intent of the present invention is, of course, to properly position and move the focal point of the cutting laser 30 through selected portions of the cataracrous tissue of lens 10 to vaporize and liquify this tissue for subsequent aspiration. How this is done is crucial because, it is extremely important that all photoablation occur within the lens 10 itself. For example, there could be grave consequences if the posterior capsule 18 were to be inadvertently perforated.

To begin the procedure of the present invention, the operator first locates the cross-over 34 of the double He-Ne beam 32 on the posterior capsule 18 of the eye. The cross-over 34 is then withdrawn in an anterior direction, i.e. from the posterior capsule 18 toward the anterior capsule 20 and cornea 36 of the eye. Specifically, the cross-over 34 is withdrawn approximately one hundred microns (100 um). This will position the cross-over 34 within the cortex 12 of lens 10 and adjacent the posterior capsule 18. The operator then activates the laser source 28 to make an incision (e.g. incision 40d) into the tissue of lens 10 beginning at the posterior capsule 18 and incising to an anterior position 20. This process is repeated until a stratum 42 of minute incisions 40 has been made adjacent the posterior capsule 18.

It happens that the photoablation process which creates the incisions 40 also generates vapors that infiltrate between the layers 16 of the cortex 12. These vapors, together with some possible consequent enzyme activity, liquify the tissue in lens 10 along the stratum 42. One consequence of this is that the refractive characteristics of the now liquified tissue is different from the as-yet untreated tissue. The operator can therefore use the stratum 42 as a reference from which to generate additional, more anterior, strata 42. Perhaps this can be better appreciated by a brief reference to FIG. 6 wherein the most posterior strata 42' is shown. The liquified tissue 64 in this strata 42' is what can be used to reference the next more anterior stratum 42 of incisions 40.

Figure 2:
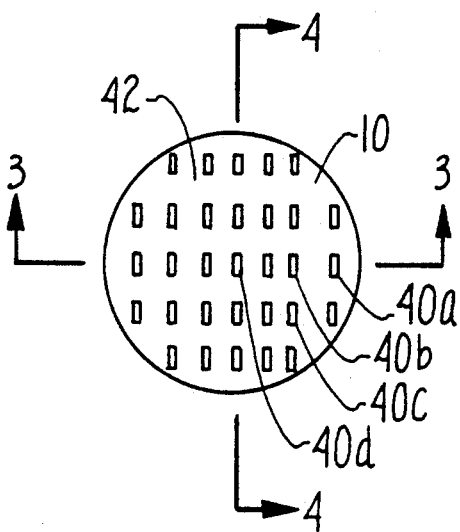
FIG. 2 is a schematic of the lens as would be seen looking along the axis of the eye at the equatorial plane of the lens.

FIG. 2 shows a stratum 42 of incisions 40 as might be created by the operator. This stratum 42 is only representative, and the various incisions might well be positioned closer to each other. Further, the incisions 40 need not necessarily be created in neatly aligned rows. It is important, however, that the most posterior stratum 42 be created in reference to the posterior capsule 18 with a withdrawal offset for safety reasons. Subsequent strata 42 can then be created with reference to previously created stratum 42 without any withdrawal requirement, and each subsequent incision in each stratum is made in the direction from a posterior to an anterior position.

Figure 3:
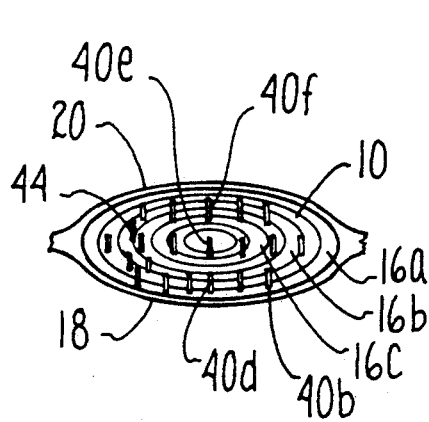
FIG. 3 is a cross sectional view of a lens as seen along the line 3—3 in FIG. 2.
Figure 4:
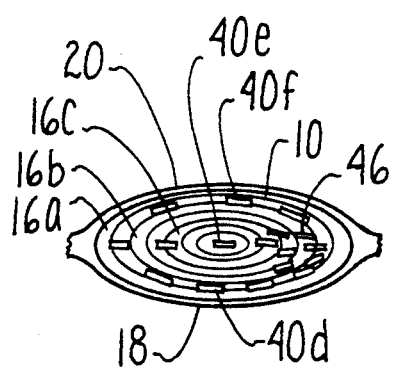
FIG. 4 is a cross sectional view of a lens as seen along the line 4—4 in FIG. 2.

FIGS. 3 and 4 together show perpendicular cross sectional views of the lens 10 with several strata 42 of incisions 40. Again, the location and relationships of the various incisions 40 and the strata 42 are only representative. The cluster 44 of incisions 40 in FIG. 3 and the cluster 46 of incisions 40 in FIG. 4 are, perhaps, more realistic. The separation between the strata 42 and the other incisions 40 is shown for clarity.

In order to better appreciate the orientation of the strata 42 and the dimensional characteristics of the incisions 40 which create the various strata 42, consider the three incisions 40d, 40e and 40f. These three incisions 40 are substantially oriented along the axis 48 of the eye, with the incision 40e located on the equator 50 of the eye. As so arranged, the incision 40d will be in the most posterior stratum 42, the incision 40e will be in the equatorial stratum 42, and the incision 40f will be in the most anterior stratum 42. As before, these are representative strata, and there will most likely be additional strata created between the most posterior and the most anterior strata.

Though, as shown in FIGS. 5A, 5B and 5C, the individual incisions 40 will have slightly different shapes for specific reasons, their dimensions have some commonality. For example, consider the contained volume of the typical incision 40e shown in FIG. 5B. The incision 40e has a length 52 which is approximately two millimeters (2 mm) and a depth or height 54 which is approximately five hundred microns (500 um). The width 56 of the incision 40e will be only a few microns. These same values will be used for corresponding dimensions in the incisions 40d and 40f.

FIGS. 5A and 5C show that the incisions 40 can be curved. More specifically, the incision 40d is shown in FIG. 5A with a radius of curvature 58 which is approximately six millimeters (6 mm). Importantly, since the incision 40d is representative of the incisions 40 in the most posterior stratum 42', the radius of curvature 58 is oriented anteriorly from the incision 40d. Thus, incision 40d is curved in a direction which conforms the convex surface of incision 40d with the posterior capsule 18 of the eye. On the other hand, but similarly, since the incision 40f is in the most anterior stratum 42, it is shown in FIG. 5C to be curved with a radius of curvature 60 that is oriented posteriorly from the incision 40f. Thus, incision 40f is curved in a direction which conforms its convex surface with the anterior capsule 20 of the eye. The incision 40e, shown in FIG. 5B has no curvature, and any incisions 40 which are between the stratum 42 of incisions 40e and the respective stratum 42 of incision 40d or 40f can have intermediate curvatures. In each case, however, the actual dimensions of a particular incision 40 in a particular stratum 42 can be preprogrammed in the laser source 28 using well known computer software techniques.

Whereas the selection of the place in the tissue of lens 10 where an incision 40 is to be made can be done manually, the actual incision 40 is done automatically. For example, the cross-over 34 is located by the operator at a point in the tissue of lens 10 as disclosed above. This will establish a start point 62, such as the start point 62 shown for incision 40d in FIG. 5A. Laser source 28 is then activated and the focal point of the cutting beam 30 moves to photoablate a volume of tissue, such as the volume represented by the incision 40d in FIG. 5A. It is to be appreciated that the particular start point 62 can be varied relative to the incision 40 according to the desires of the operator and preprogrammed instruction. As examples, the start points 62' and 62" are respectively shown for the incisions 40e and 40f.

Due to the fact that less tissue is being crossed by the cutting beam 30 as the more anterior strata 42 are created, the power requirements for the beam 30 can be reduced. For example, the initial power required for photoablating incisions 40 into the most posterior stratum 42' will be approximately four hundred microjoules (400 uj) per pulse. This level of power can be reduced by approximately seventy five microjoules (75 uj) for each more anterior stratum 42. Further, it may be desirable to reduce relative power for incisions 40 near the axis 48 as compared to the more peripheral incisions which are farther away from the axis 48.

The FIGS. 6 and 7 respectively show a lens 10 which has been partially liquified, and the same lens 10 with substantially all of the cataractous tissue liquified. Once the lens 10 has been treated, the liquified tissue 64 can be removed. To do this, an aspirator 66 is inserted through the sclera 66 and into the lens capsule, through the anterior capsule 20, to aspirate the liquified tissue 64. Typically, a plastic or acrylic lens is then surgically positioned in the capsule to restore sight for the patient. It is possible, with the present invention, that a liquid, rather than a plastic lens, may be used to replace the cataractous tissue 64 which has been removed from the lens capsule.

While the particular method for removing cataractous tissue from the lens capsule of an eye as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A method for using a cutting beam of laser light to remove cataractous tissue from the lens capsule of an eye which comprises the steps of:
    selectively focusing an energized beam of the laser light into the lens of the eye to make a plurality of minute incisions within the tissues of the lens of the eye to successively photoablate a plurality of strata of the lens tissue, the strata being successively photoablated in a posterior-anterior direction;
    allowing vapors from the photoablation step to infiltrate between the layers of the lens cortex to fragment and liquify the lens tissues; and
    aspirating the liquefied lens tissue from the lens capsule.

2. A method as recited in claim 1 wherein the step of making the most posterior stratum comprises the steps of:
    locating the cross-over of a double He-Ne light beam onto a posterior capsule of the eye;
    withdrawing the cross-over in an anterior direction approximately 100 um to position the cross-over at a start point in the lens tissue adjacent the posterior capsule;
    focusing the cutting laser beam to be coincident with the cross-over;
    moving the focal point of the cutting laser beam to make an incision; and
    relocating the cross-over on the posterior capsule, withdrawing the cross-over, focusing the cutting laser, and moving the focal point as desired to make additional incisions in the most posterior stratum.

3. A method as recited in claim 2 further comprising the steps of:
    locating the cross-over of the double He-Ne beam, and the coincident focal point of the cutting laser beam, on a previously accomplished stratum of incisions to establish a start point;
    moving the focal point of the cutting laser beam from the start point to make a minute incision into the lens tissue;
    making additional incisions into the lens tissue to create a stratum of incisions; and
    creating additional stratum of incisions throughout the cortex and nucleus of the lens, as necessary, to liquify the lens tissue.

4. A method as recited in claim 3 wherein an incision is made by moving the focal point of the cutting laser beam along a path, which begins at the start point and which is approximately two millimeters (2 mm) in length and approximately five hundred microns (500 um) in depth.

5. A method as recited in claim 4 wherein each incision in the most posterior stratum of incisions is curved with an anterior radius of curvature of approximately six millimeters (6 mm).

6. A method as recited in claim 5 further comprising the step of varying the radius of curvature of the incisions from stratum to stratum to transition from an anterior concave curve, through a substantially uncurved incision in the stratum along the equator of the lens, and to and anterior convex curve for the most anterior stratum, the incisions in the most anterior stratum having a posterior radius of curvature of approximately six millimeters (6 mm).

7. A method as recited in claim 6 wherein each incision in the most posterior stratum of incision is made using a cutting laser beam having approximately four hundred microjoules (400 uj) of laser energy at the focal point.

8. A method as recited in claim 7 further comprising the step of reducing the laser energy of the cutting laser beam by approximately seventy-five microjoules (75 uj) for the creation of each successive more anterior stratum of incisions.

9. A method as recited in claim 8 wherein the aspiration of liquified tissue from the lens capsule is accomplished using a hollow needle.

10. A method as recited in claim 9 wherein each incision within each stratum is made in the direction from a posterior to an anterior position.

11. A method for removing cataractous lens tissue from the lens capsule of an eye having a posterior capsule and an anterior capsule which comprises the steps of:
    distancing the focal point of a cutting laser beam, in an anterior direction from the posterior capsule of the lens, to make series of incisions in the posterior cortex layer of the lens;
    referencing previously incised portions of the lens to make additional incisions in the cortex and nucleus of the lens to liquify the lens tissue; and
    aspirating the liquified lens tissue from the lens capsule.

12. A method as recited in claim 11 wherein the step of distancing the focal point from the posterior capsule comprises the steps of:
    locating the cross-over of a double He-Ne light beam onto the posterior capsule of the eye; and
    withdrawing the cross-over in an anterior direction approximately 100 um to position the cross-over at a start point in the lens tissue adjacent the posterior capsule.

13. A method as recited in claim 12 wherein the step of referencing previously incised portions of the lens is accomplished by stratifying the incisions to stack the resultant strata in a posterior-anterior direction.

14. A method as recited in claim 13 the referencing step further comprises the steps of:
   locating the cross-over of the double He-Ne beam, and the coincident focal point of the cutting laser beam, on a previously accomplished stratum of incisions to establish a start point;
   moving the focal point of the cutting laser beam from the start point to make a minute incision into the lens tissue;
   making additional incisions into the lens tissue to create a stratum of incisions; and
   creating additional stratum of incisions throughout the cortex and nucleus of the lens, as necessary, to liquify the lens tissue.

15. A method as recited in claim 14 further comprising the step of allowing the vapors created by the incisions to infiltrate between the layers of the len cortex to fragment and liquify the lens tissues.

16. A method as recited in claim 15 wherein an incision is made by moving the focal point of the cutting laser beam along a path, which begins at the start point and which is approximately two millimeters (2 mm) in length and approximately five hundred microns (500 um) in depth.

17. A method as recited in claim 16 further comprising the step of varying the radius of curvature of the incisions from stratum to stratum to transition from an anterior concave curve in the most posterior stratum, through a substantially uncurved incision in the stratum along the equator of the lens, and to an anterior convex curve for the most anterior stratum, the incisions in the most posterior stratum having an anterior oriented radius of curvature of approximately six millimeters (6 mm) and the incisions in the most anterior stratum having a posterior oriented radius of curvature of approximately six millimeters (6 mm).

18. A method as recited in claim 17 wherein each incision in the most posterior stratum of incision is made using a cutting laser beam having approximately four hundred microjoules (400 uj) of laser energy at the focal point and the method further comprises the step of reducing the laser energy of the cutting laser beam by approximately seventy-five microjoules (75 uj) for the creation of each successive more anterior stratum of incisions.

19. A method as recited in claim 18 wherein the aspiration of liquified tissue from the lens capsule is accomplished using a hollow needle.

20. A laser phacofragmentation method for removing cataractous tissue from the lens of an eye having a posterior capsule and an anterior capsule using an ophthalmic laser apparatus which comprises the steps of:
   a) locating the cross-over of a double He-Ne light beam onto the posterior capsule of the eye, the focal point of a cutting laser beam being coincident with the cross-over;
   b) withdrawing the cross-over in an anterior direction approximately 100 um from the posterior capsule to position the cross-over at a start point in the lens tissue adjacent the posterior capsule;
   c) moving the focal point of the cutting laser beam (i.e. cross-over) along a path, which begins at the start point, to make an incision into the lens tissue which is approximately 2 mm in length, approximately 500 um in depth (measured anteriorly from the start point), and which is curved with an anterior radius of curvature of approximately 6 mm;
   d) repeating steps a) and b) to reposition the focal point of the cutting laser beam at a new start point which is substantially adjacent the immediately preceding start point;
   e) repeating step c) to make an incision which is substantially parallel to the immediately preceding incision;
   f) repeating steps d) and e), as desired and necessary, to vaporize and liquefy a layer of lens tissue;
   g) focusing the cutting laser beam at a start point on the previously liquified layer of lens tissue;
   h) moving the focal point of the cutting beam along a path, which begins at the start point, to make an incision into the lens tissue which is approximately two millimeters (2 mm) in length and approximately five hundred microns (500 um) in depth;
   i) repeating steps g) and h), as necessary and desired to vaporize and liquefy a layer of lens tissue; and
   j) repeating step i, as desired, to vaporize and liquefy substantially all of the lens tissue.

21. A method as recited in claim 20 wherein incisions into the lens tissue are made by stratifying the incisions to stack the resultant strata in a posterior-anterior direction, and wherein the radius of curvature of the incisions is varied from stratum to stratum to transition from an anterior concave curve in the most posterior stratum, through substantially uncurved incisions in the stratum along the equator of the lens, and to an anterior convex curve for the most anterior stratum, the incisions the most posterior stratum having an anterior oriented radius of curvature of approximately six millimeters (6 mm) and the incisions in the most anterior stratum having a posterior oriented radius of curvature of approximately six millimeters (6 mm).

22. A method as recited in claim 21 wherein each incision in the most posterior stratum of incision is made using a cutting laser beam having approximately four hundred microjoules (400 uj) of laser energy at the focal point and the method further comprises the step of reducing the laser energy of the cutting laser beam by approximately seventy-five microjoules (75 uj) for the creation of each successive more anterior stratum of incisions.

23. A method as recited in claim 22 wherein liquified tissue from the lens capsule is aspirated using a hollow needle.

* * * * *